(12) United States Patent
Zaczek

(10) Patent No.: US 6,262,081 B1
(45) Date of Patent: Jul. 17, 2001

(54) COMPOSITION FOR AND METHOD OF TREATING NEUROLOGICAL DISORDERS

(75) Inventor: Robert Zaczek, Avondale, PA (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/349,906

(22) Filed: Jul. 8, 1999

Related U.S. Application Data
(60) Provisional application No. 60/092,341, filed on Jul. 10, 1998.

(51) Int. Cl.[7] .......................... A61K 31/445; A61K 31/44
(52) U.S. Cl. .......................... 514/332; 514/297; 514/317; 514/333
(58) Field of Search ...................................... 514/332, 333, 514/317, 297

(56) References Cited

U.S. PATENT DOCUMENTS

| | | |
|---|---|---|
| 4,760,083 | 7/1988 | Myers et al. . |
| 4,895,841 | 1/1990 | Sugimoto et al. . |
| 5,173,489 | 12/1992 | Earl et al. . |
| 5,750,528 | 5/1998 | Aiken et al. . |

FOREIGN PATENT DOCUMENTS

| | | |
|---|---|---|
| 0311010A | 4/1989 | (EP) . |
| 9200760 | 1/1992 | (WO) . |
| 9424131A | 10/1994 | (WO) . |
| 9517154 | 6/1995 | (WO) . |
| 9527489A | 10/1995 | (WO) . |
| 9529909 | 11/1995 | (WO) . |
| 9722339 | 6/1997 | (WO) . |

OTHER PUBLICATIONS

Budavari, S., Editor, et al, The Merck Index, Twelfth Edition, p. 1546, entry No. 9199, 1996.*
Earl, Richard A. et al., "2–Fluoro–4–pyridinylmethyl Analogs of Linopirdine . . . ", J. Med. Chem. (1998), 41(23), 4615–4622, XP002145541.
Zaczek, R. et al., "Two new potent neurotransmitter release enhancers . . . ", J. Pharmacol. Exp. Ther. (1998), 285(2), 724–730, XP002145542.
Wilkerson, W.W. et al., "Acetylcholine release enhancers related to linopirdine . . . ", Eur. J. Med. Chem. (1996), 31(4), 319–330, XP002145543.
*The New England Journal of Medicine*, Cotzias et al., vol. 276, pp. 374–379 (1967).
*Drug Development Research*, Nickolson et al., vol. 19, pp. 285–300 (1990).
*Neuroscience Letters*, Zaczek et al. (1993).
*Drug Development Research*, Zaczek et al., vol. 29, pp. 203–208 (1993).
*Remington's Pharmaceutical Sciences*, Gennaro ed., Mack Publishing Company, Easton, PA (1985).

* cited by examiner

*Primary Examiner*—William R. A. Jarvis
(74) *Attorney, Agent, or Firm*—Kenneth B. Rubin; Kalim S. Fuzail

(57) ABSTRACT

The invention relates to a method of treating neurological disorders associated with neurotransmitter deficit in a mammal comprising administering to the mammal a therapeutically effective amount of a combination of: (i) at least one neurotransmitter release enhancer, and (ii) at least one acetylcholinesterase inhibitor. The invention also relates to compositions and kits containing the same.

19 Claims, No Drawings

COMPOSITION FOR AND METHOD OF TREATING NEUROLOGICAL DISORDERS

This application claims the benefit of U.S. Provisional Application No. 60/092,341 filed on Jul. 10, 1998.

FIELD OF THE INVENTION

This invention relates to a method of treating neurological disorders associated with neurotransmitter deficit in a mammal comprising administering to the mammal a therapeutically effective amount of a combination of: (i) at least one neurotransmitter release enhancer and (ii) at least one acetylcholinesterase inhibitor. This invention also relates to compositions and kit containing the same.

BACKGROUND OF THE INVENTION

The hypothesis that the symptoms of neurodegenerative diseases such as Alzheimer's Disease are the result of reduced neuronal function has led to the development of therapies aimed at reversing these deficits. In an attempt at neurotransmitter replacement, neurotransmitter precursor supplementation has been used to treat neurodegenerative diseases. Cotzias, et al. *New Engl. J. Med.* 276:374–379 (1967).

Another means of enhancing neurotransmission is to increase stimulated, but not basal, release of neurotransmitters, thereby specifically increasing normal synaptic activity. Substituted oxindoles such as 3,3-bis(4-pyridinylmethyl)-1-phenylindolin-2-one are agents under investigation as a palliative treatment for the dementia associated with Alzheimer's disease. Compounds of this structural type have been shown to enhance potassium($K^+$)-stimulated release of tritium from rat brain slices preloaded with [$^3$H]choline, [$^3$H]dopamine, and [$^3$H]serotonin without affecting basal efflux. Nickolson et al., *Drug Dev. Res.* 19:285–300 (1990); Zaczek et al. *Neurosci. Lett.* (1993); Zaczek et al., *Drug Dev. Res.* 29:203–208 (1993).

The present invention is based on a synergy found with a combination therapy involving neurotransmitter release enhancers, and acetylcholinesterase inhibitors. Such a therapy provides higher extracellular levels of acetylcholine and a greater improvement for the treatment of neurological disorders such as Alzheimer's disease.

SUMMARY OF THE INVENTION

The present invention provides a method of treating neurological disorders associated with neurotransmitter deficit in a mammal comprising administering to the mammal a therapeutically effective amount of a combination of: (i) at least one neurotransmitter release enhancer, such as a compound of Formula (I) (shown below); and (ii) at least one acetylcholinesterase inhibitor. The present invention is also directed to pharmaceutical compositions and pharmaceutical kits containing the same.

DETAILED DESCRIPTION OF THE INVENTION

This present invention provides a method of treating neurological disorders associated with neurotransmitter deficit in a mammal comprising administering to the mammal, in combination, a therapeutically effective amount of: (i) at least one neurotransmitter release enhancer, such as of the Formula (I) (shown below); and (ii) at least one acetylcholinesterase inhibitor.

In the present invention, it has been discovered that the administration of a neurotransmitter release enhancer such as of Formula (I) (component (i)) in combination with an acetylcholinesterase inhibitor precursor (component (ii)) may result in an unexpected synergistic effect in providing higher extracellular levels of acetylcholine. Thus, the amount of acetylcholine which is released when a neurotransmitter release enhancer is administered in combination with an acetylcholinesterase inhibitor is at least additive over each agent when administered alone. This additive and believed to be synergistic combination is expected to greatly increase the efficacy of single agent or multiple agent treatments of neurological disorders associated with neurotransmitter deficits, such as Alzheimer's Disease, disorders which are associated with acetylcholine deficits.

Thus, it has been discovered that the neurotransmitter release enhancers useful in the present invention may be administered in combination with an acetylcholinesterase inhibitor, thereby reducing the doses of each drug required to achieve the amounts of neurotransmitter, such as acetylcholine, released. Moreover, it has been discovered that the use of the compounds of component (i) and component (ii) of the invention in combination results in a greater than additive acetylcholine releasing effect over component (i) alone. Thus, the combination treatment of the present invention of components (i) and (ii) permits the use of lower doses of each component, with reduced adverse, toxic effects of each component. It also provides for a greater window of efficacy, since the same maximum tolerated doses can be administered before toxic effects associated with each agent are observed. A lower dosage minimizes the potential of side effects of the compounds, thereby providing an increased margin of safety relative to the margin of safety for each component when used as a single agent.

As used herein, the term "neurotransmitter release enhancer" or "neurotransmitter release enhancing agent" refers to compounds or compositions which serve to increase the cellular release of one or more neurotransmitters and includes the compounds of Formula (I) described below. The neurotransmitter release enhancer compounds of Formula (I) are also described in U.S. Pat. No. 4,760,083, U.S. Pat. No. 5,173,489, the disclosures of each of which are hereby incorporated herein by reference in their entirety. Other compounds and compositions are known and will be readily apparent to those skilled in the art, once armed with the present disclosure. Such neurotransmitter release enhancers may serve to increase the cellular release of one or more neurotransmitters, such as, for example, the neurotransmitters dopamine, acetylcholine, choline, serotonin, noradrenaline, adrenaline and glutamic acid. Preferably, the neurotransmitter release enhancers serve to increase the release of acetylcholine, and are preferably the compounds of Formula (I).

The phrase "acetylcholinesterase inhibitor", as used throughout, refers to compounds which inhibit the acetylcholinesterase enzyme.

By "therapeutically effective amount" it is meant an amount of component (i) and component (ii) that when administered alone or in combination to a mammal is effective to treat the neurological disorder, such as by increasing the amount of the neurotransmitter(s) in deficit, especially the neurotransmitter acetylcholine.

By "administered in combination", or the like, when referring to component (i) and component (ii) of the present invention, it is meant that the components are administered concurrently to a mammal being treated. By concurrently, it is meant that each component may be administered at the same time or sequentially in any order at different points in time, however if not administered at the same time, they should be administered sufficiently closely in time so as to provide the desired treatment effect. Suitable dosing intervals and dosing order with such compounds will be readily apparent to those skilled in the art, once armed with the present disclosure. Preferably, all components are administered at the same time, and if not administered at the same time, preferably they are all administered less than one hour apart from one another.

The present invention also includes pharmaceutical compositions (that is, combination products), such pharmaceutical compositions (combination products) comprising or consisting essentially of, in combination, a neurotransmitter release enhancing compound (such as Formula (I)), and an acetylcholinesterose inhibitor. Such compositions may be in solid or liquid dosage units, and may further include a suitable pharmaceutical carrier.

The present invention also includes pharmaceutical kits comprising or consisting essentially of a neurotransmitter release enhancer (such as compound of Formula (I)), together with an acetylcholinesterase inhibitor. In the kit, the neurotransmitter release enhancer and acetylcholinesterase inhibitor may each be presented in separate vials as compounds, and/or in separate vials as compounds in combination with a pharmaceutically acceptable carrier. Alternatively, one or more of the neurotransmitter release enhancers and acetylcholinesterase inhibitors may be combined together in one or more vials, with or without a carrier. Thus, for example, the invention includes pharmaceutical kits comprising a separate vial comprising the neurotransmitter release enhancer compound of Formula (I), and a separate vial comprising acetylcholinesterase inhibitor, each vial also containing, if desired, a carrier.

The compositions and kits of the present invention may be employed in the treatment of neurological diseases characterized by deficit levels (that is, abnormally low levels) of a neurotransmitter, such as, for example, acetylcholine. Such diseases are well known and include, for example, Alzheimer's Disease, as well as other central nervous system disorders or degenerative diseases. The compositions and kits may also be employed for the standardization of biochemical assays dependant on defined levels of released neurotransmitters, such as acetylcholine.

In the method of the present invention, the neurotransmitter release enhancing compound (such as a compound of Formula (I)) may be administered in combination with an acetylcholinesterase inhibitor to achieve a synergistic increase in acetylcholine. Synergy occurs when the effect (such as release of the neurotransmitter acetylcholine) of the compounds when administered in combination is greater than the additive effect of the compounds when administered alone as a single agent. In general, a synergistic effect is most clearly demonstrated at suboptimal concentrations of the compounds.

The method of the present invention provides for an enhanced effect of the two drugs when administered in combination. Thus, the claimed combination treatment allows for the use of lowered clinical doses and increases the window of efficacy. In view of the marginal effects associated with the presently approved therapies for treating diseases characterized by abnormally low levels of brain neurotransmitters like acetylcholine, such as Alzheimer's Disease, the present invention provides an important advantage over current therapies.

Acetylcholinesterase inhibitors useful in the present invention include tacrine (a tetrahydroacridine) and compounds described in U.S. Pat. No. 4,895,841, particularly the compound donepezil HCl sold under the tradename ARICEPT.

As discussed in U.S. Pat. Nos. 4,760,083 and 5,173,489, compounds of the α,α-disubstituted ring systems of Formula (I) represent a new class of neurotransmitter release enhancers which are useful for the treatment of diseases characterized by abnormally low levels of brain neurotransmitter acetylcholine, such as Alzheimer's Disease. In certain instances, the compounds disclosed were also found to enhance the release of dopamine.

The neurotransmitter release enhancers of component (i) useful in this invention include α,α-disubstituted ring systems of the Formula (I):

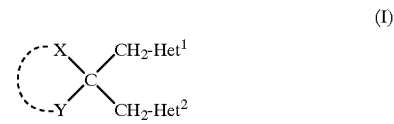

(I)

or a pharmaceutically acceptable salt thereof, wherein X and Y are taken together to form a saturated or unsaturated carbocyclic first ring and the shown carbon in said ring is α to at least one additional carbocyclic aromatic ring fused to the first ring, the total number of carbocyclic fused rings being 3–5, the sole heterocyclic substituents on said fused rings being $Het^1$ and $Het^2$; and one of $Het^1$ or $Het^2$ is 2, 3, or 4-pyridyl or 2, 4, or 5-pyrimidinyl and the other is selected from
  (a) 2, 3, or 4-pyridyl
  (b) 2, 4, or 5-pyrimidinyl,
  (c) 2-pyrazinyl,
  (d) 3 or 4-pyridazinyl,
  (e) 3 or 4-pyrazolyl,
  (f) 2 or 3-tetrahydrofuranyl, and
  (g) 3-thienyl.

Preferred compounds of component (i) useful in the present invention are compounds of Formula (Ia):

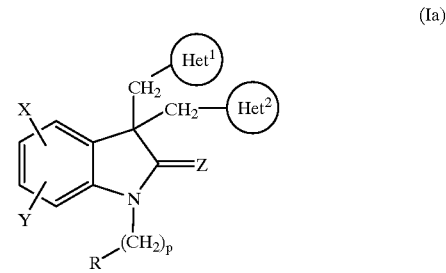

(Ia)

wherein:
  p is 0 or 1;
  Z is O or S;
  R is $C_1$–$C_{10}$ alkyl, $C_3$–$C_8$ cycloalkyl, 2-pyridyl, 3-pyridyl, 4-pyridyl, or

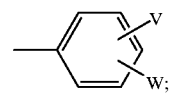

V,W,X, and Y independently are H, halo, $C_1$–$C_3$ alkyl, $OR^1$, $NO_2$, $CF_3$, CN or $NR^1R^2$;

$R^1$ and $R^2$ independently are H or $C_1-C_3$ alkyl;

$Het^1$ and $Het^2$ independently are 6-membered heterocyclic aromatic rings containing one or two nitrogen atoms as part of the ring optionally substituted with one substituent selected from the group $C_1-C_3$ alkyl, halo, $OR^1$ or $NR^1R^2$; or an N-oxide or pharmaceutically acceptable acid addition salt thereof.

Also preferred compounds of component (i) useful in the method of the present invention are compounds of Formula (Ib):

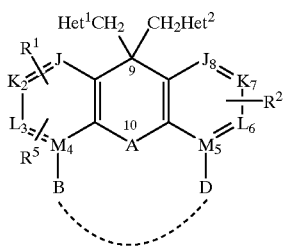
(Ib)

or a pharmaceutically acceptable salt thereof, wherein:

each J, K, L and M independently are N, $CR^1$, $CR^5$ or $CR^2$ with the proviso that when either $M_4$, $M_5$ or both is N, then B, D or both cannot be $R^1$ or $R^2$;

A is $(CH_2)_n$, $C(=S)$, O, $S(O)_1$, $S(O)_2$, S, $NR^3$, $-CH=CH-$, $-C(=O)-$, $-CH(OR^3)-$, $C(=NOH)-$,

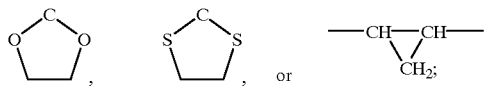

n is 0, 1, 2 or 3;

$R^1$ and $R^2$ independently are H, halo, alkyl of 2–3 carbon atoms, acetyl, $OR^3$, $NO_2$, CN, $NR^3R^4$, or fluoroalkyl of 1–3 carbon atoms;

$R^3$ and $R^4$ independently are H, alkyl of 1–3 carbon atoms, or acyl;

B and D independently are $R^1$ or $R^2$ or, when A is $(CH_2)_o$, can be taken together to form $-CH=CH-$, or $-CH_2-CH_2-$;

$R^5$ independently is H, or is taken together with $R^1$ to form a 2,3- or a 3,4-fused benzo ring;

one of $Het^1$ or $Het^2$ is 2, 3, or 4-pyridyl or 2, 4 or 5-pyrimidinyl and the other is selected from:
(a) 2, 3 or 4-pyridyl,
(b) 2, 4, or 5-pyrimidinyl,
(c) 2-pyrazinyl,
(d) 3 or 4-pyridazinyl,
(e) 3 or 4-pyrazolyl,
(f) 2 or 3-tetrahydrofuranyl, and
(g) 3-thienyl.

Also preferred compounds of component (i) useful in the present invention are compounds of Formula (Ic):

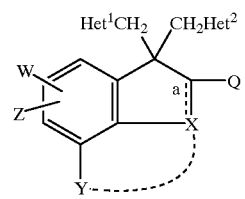
(Ic)

or a pharmaceutically acceptable salt thereof, wherein;

a is a single bond or double bond;

X and Y taken together when a is a single bond is

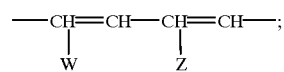

X and Y taken together when a is a double bond is

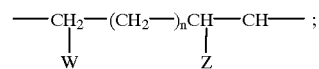

where n is 1 or 2;

Q when a is a single bond is $=O$; $=S$; $H_2$, $=NOR^1$, $-O(CH_2)_pO-$, $-S(CH_2)_pS-$, $-(H)F$, $=NOR^1$, $F_2$; $(R^1)OR^3$, $=CR^1R^2$;

Q, when a is a double bond is $R^2$, $OR^3$ or halo;

p is 2 or 3;

$R^1$ is H, alkyl of 1–10 carbon atoms, cycloalkyl of 3–8 carbon atoms, or

$R^2$ is $R^1$, $NO_2$, CN, $CO_2R^1$, $C(=O)R^1$ or halo;

$R^3$ is $C(=O)R^1$ or $CR^1$;

W, Z independently are H, halo, alkyl of 1–3 carbon atoms, $OR^3$, $NO_2$, $CF_3$, fluoroalkyl, CN, or $N(R^1)_2$; and one of $Het^1$ or $Het^2$ is 2, 3, or 4-pyridyl or 2, 4, or 5-pyrimidinyl and the other is selected from
(a) 2, 3, or 4-pyridyl,
(b) 2, 4, or 5-pyrimidinyl,
(c) 1-pyrazinyl,
(d) 3 or 4-pyridazinyl,
(e) 3 or 4-pyrazolyl,
(f) 2 or 3-tetrahydrofuranyl, and
(g) 3-thienyl.

Also preferred compounds of component (i) useful in the present invention are compounds of Formula (Id):

(Id)

[Structure of Formula (Id) showing Het¹CH₂ and CH₂Het² substituents on a bicyclic ring system with W, Z, Y, Q, X, A, V, a, b labels]

or a pharmaceutically acceptable salt thereof, wherein:
a is a single bond or double bond;
b is a single bond or double bond, provided one of a or b is a single bond;
X independently when a and b are single bonds is: O,S, $CR^1R^2$, CQ, $CR^1OR^3$ or —(CH₂)N— where N is 1–3, $N(CH_2)_pR^3$ where p is 0–1, or $NC(=O)R^1$;
X independently when one of a or b is a double bond is $CR^2$, $COR^3$, or N;
V independently when b is a single bond is CQ;
V independently when b is a double bond is CR2 or COR3;
A is a single bond, $—(—CR_2^1—)_n—$, —X—, $—(—CR_2^1—)_n—X$, where n is 1, 2 or 3 and X is as defined above when a is a single bond;
Y and V taken together when A and b are single bonds is $$—\underset{W}{C}=\underset{Z}{C}—CH=CH—;$$

Y and V taken together when A is a single bond is —CH₂—(CH₂)m—CH₂— where m is 1 or 2; provided that when Y and V are connected, then V and X are not connected;
V and X taken together when b is a double bond is C—CH=CH—CH=CH—C—, or, C—(—CH₂—)$_p$—C; provided that when V and X are connected, then Y and V are not connected;
Q when a is a single bond is =O, =S, H₂, =NOR¹, —O(CH₂)$_p$O—, —S(CH₂)$_p$S—, —(H)F, F², (R¹)OR³, =CR¹R²;
Q when a is a double bond is R², OR³ or halo;
p is 2 or 3;
R¹ is H, alkyl of 1–10 carbon atoms, cycloalkyl of 3–8 carbon atoms, or

[Structure showing phenyl ring with W and Z substituents]

R² is R¹, NO₂, CN, CN₂R¹, C(=O)R¹ or halo;
R³ is R¹ or C(=O)R¹;
W, Y, Z independently are H, halo, alkyl of 1–3 carbon atoms, OR³, NO₂, CF₃, fluoroalkyl, CN, or N(R¹)₂; and
one of Het¹ or Het² is 2, 3, or 4-pyridyl or 2, 4, or 5-pyrimidinyl and the other is selected from
(a) 2, 3, or 4-pyridyl,
(b) 2, 4, or 5-pyrimidinyl,
(c) 2-pyrazinyl,
(d) 3, or 4-pyridazinyl,
(e) 3, or 4-pyrazolyl,
(f) 2, or 3-tetrahydrofuranyl, and
(g) 3-thienyl.

More preferred compounds of component (i) useful in the present invention are compounds of Formula (I) wherein:
Het¹ or Het² is 2-, 3-, or 4-pyridyl or 2-, 4-, or 5-pyrimidinyl and the other is 2-, 3-, or 4-pyridinyl, 2-, 4-, or 5-pyrimidinyl, or 2-, or 3-tetrahydrofuranyl.

Most preferred compounds of component (i) useful in the present invention are compounds of Formula (I) wherein:
Het¹ and Het² is most preferably selected from:
(a) 4-pyridinyl and 4-pyridazinyl,
(b) 4-pyrimidinyl and 4-pyrimidinyl,
(c) 4-pyridinyl and 4-pyrimidinyl,
(d) 4-pyridinyl and 3-tetrahydrofuranyl.

Preferred compounds of component (i) useful in the present invention are the compounds of Formula (Ia) wherein:
p is 0;
Z is O;
W, X, Y and Z are hydrogen;
R is methyl, phenyl or m-chlorophenyl; and
Het¹ and Het² are each pyridinyl attached by a ring carbon atom.

Preferred compounds of component (i) of the present invention also include compounds of Formula (V):

Formula (V)

[Structure of Formula (V) showing an anthracenone system with Het-1 and Het-2 substituents at the 10-position, R² and R³ substituents on the aromatic rings, A position, and ketone (O) group]

and pharmaceutically acceptable salt or prodrug forms thereof, wherein:
A is N or CH;
Het-1 and Het-2 are each independently selected from 2-pyridyl, 3-pyridyl or 4-pyridyl substituted with X;
R² and R³ are independently selected from H, F, Cl, Br, I, CF₃, R⁴, or —C≡CH;
R⁴ is alkyl of 1 to 4 carbons;
X in each instance is independently selected from H, F, Cl, Br, I, or CF₃, provided that at least one X is other than H.

Preferred compounds of Formula (V) are compounds wherein:
Het-1 and Het-2 are independently 4-pyridyl substituted with X; and/or
A is CH; and/or
R² and R³ are independently H, F, Br, or CF₃.
Preferred compounds of Formula (V) are those wherein one X is H and the other F; and R² and R³ are each H.
Preferred compounds of Formula (V) also include those wherein each X is F and R² and R³ are each H.
Preferred compounds of Formula (V) are 10-((2-fluoro-4-pyridyl)methyl)-10-(4-pyridylmethyl)-9(10H)-anthracenone and 10,10-bis((2-fluoro-4-pyridyl)methyl)-9(10H)-anthracenone.

Preferred compounds of component (i) useful in the present invention include: 3,3-bis(4-pyridinylmethyl)-1-phenylindolin-2-one; 3,3-bis(4-pyridinylmethyl)-1-phenylindolin-2-one; and 10,10-bis(2-fluoro-4-pyridinyl)methyl)-9(10H) anthracenone.

Methods for the preparation of the compounds of Formula (I) are described in great detail in Myers et al., U.S. Pat. No. 4,760,083 and Earl et al., U.S. Pat. No. 5,173,489, and U.S. patent application Ser. No. 08/216,881 filed Mar. 28, 1994, all of which are incorporated herein by reference in their entirety.

The preferred compound of component (ii) useful in the present invention is the compound donepezil, preferably donepezil HCl Component (i) of the present invention may also be provided as a pharmaceutical composition comprising an therapeutically effective amount of a compound of Formula (I) (including those of the subformulae Ia, Ib, Ic and Id) and a pharmaceutically acceptable carrier. Component (ii) of the present invention may likewise be presented as a pharmaceutical composition comprising a therapeutically effective amount of an acetylcholinesterase inhibitor and a pharmaceutically acceptable carrier. Mixtures of the components (i) and (ii) with or without a pharmaceutically acceptable carrier, are also within the ambit of the present invention.

Neurological disorders associated with neurotransmitter deficit include, but are not limited to Alzheimer's Disease, as well as other central nervous system disorders or degenerative diseases.

When any variable occurs more than one time in any constituent in formula (I), or any other formula herein, its definition on each occurrence is independent of its definition at every other occurrence. Also combinations of substituents and/or variables are permissable only if such combinations result in stable compounds.

As used herein, "alkyl" is intended to include both branched and straight-chain saturated aliphatic hydrocarbon groups having the specified number of carbon atoms. As used herein "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl and cyclooctyl; and "biycloalkyl" is intended to include saturated bicyclic ring groups such as [3.3.0] bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynl, propynyl and the like. "Cycloalkyl-alkyl" is intended to include cycloalkyl attached to alkyl. "Halogen" as used herein refers to fluoro, chloro, bromo, and iodo; and "counterion" is used to represent a small, negatively charged species such as chloride; bromide, hydroxide, acetate, sulfate, and the like.

As used herein, "aryl" or "aromatic residue" is intended to mean phenyl or naphthyl; "carbocyclic" is intended to mean any stable 5- or 7-membered monocyclic or bicyclic or 7- to 14-membered bicyclic or tricyclic carbon ring, any of which may be saturated, partially unsaturated or aromatic, for example, indanyl or tetrahydronaphthyl (tetralin).

As used herein, "aralkyl" is intended to mean any aryl group bearing the alkyl group. The aralkyl group may be attached at any of its carbon atoms.

The term "substituted", as used herein, means that one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious therapeutic agent.

As used herein, "pharmaceutically acceptable salts" refer to derivatives of the disclosed compounds that are modified by making acid or base salts. Examples include, but are not limited to, mineral or organic acid salts of basic residues such as amines; alkali or organic salts of acidic residues such as carboxylic acids.

As used herein, "therapeutically effective amount" means the amount capable of achieving the desired clinical effect.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Dosage and Formulation

The neurotransmitter release enhancer (component (i)), and acetylcholinesterase inhibitor (component (ii)) combination treatment of the invention can be administered by any conventional means available for the use in conjunction with pharmaceuticals, either as individual separate dosage units administered simultaneously or concurrently, or in a physical combination of each component therapeutic agent in a single or combined dosage unit. The active agents can be administered alone, but are generally administered with a pharmaceutical carrier selected on the basis of the chosen route of administration and standard pharmaceutical practice. In general, the weight ratio of component (i) to component (ii) will be in the range of 1:1 to 1:100, preferably 1:1 to 1:50.

The dosage administered will, of course vary depending on the use and known factors such as the pharmacodynamic characteristics of the particular agent, and its mode and route of administration; age, health, and weight of the recipient; nature and extent of symptoms, kind of concurrent treatment, frequency of treatment, and the effect desired. The recipient may be any type of mammal, but is preferably a human.

For use in the treatment of diseases characterized by abnormally low levels of acetylcholine, such as Alzheimer's disease, by way of general guidance, a daily oral dosage of active ingredient(s) can be about 0.001 to 1000 mg/kg of body weight. Ordinarily a dose of 0.1 to 500 mg/kg per day in divided doses one to four times a day or in sustained release form is effective to obtain the desired results.

Dosage forms (compositions) suitable for administration contain about 1 milligram to 100 milligrams of active ingredient per unit. In these pharmaceutical compositions, the active ingredient will ordinarily be present in an amount of about 0.5–95% by weight based on the total weight of the composition.

The active ingredient may be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers and methods of preparing pharmaceutical dosage forms are described in *Remington's Pharmaceutical Sciences*, Mack Publishing Company, a standard reference text in this field.

Useful pharmaceutical compositions (dosage forms) for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Suspension

An aqueous suspension is prepared for oral administration so that each 5 ml contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection is prepared by stirring 1.5% by weight of active ingredient in 10% by volume propylene glycol and water. The solution is sterilized by commonly used techniques.

Each therapeutic agent component of this invention can independently be in any dosage form, such as those described above, and can also be administered in various ways, as described above. The component (i) and (ii) of the invention may be formulated together, in a single dosage unit (that is, combined together in one capsule, tablet, powder, or liquid, etc.) as a composition (combination product). More preferably, components (i) and (ii) are formulated together as a composition. When component (i) and component (ii) are not formulated together in a single dosage unit, the neurotransmitter release enhancer component (i) may be administered at the same time as component (ii) or in any order. For example, component (i) of this invention may be administered first, followed by administration of component (ii), or they may be administered in the reverse order. When not administered at the same time, preferably the administration of component (i) and component (ii) occurs less than about one hour apart. Preferably, the route of administration of component (i) and component (ii) is oral. The terms oral agent, oral release enhancer, oral compound, or the like, as used herein, denote compounds which may be orally administered. Although it is preferable that component (i) and component (ii) of the invention are both administered by the same route (that is, for example, both orally) or in the same dosage form (that is, for example, as a tablet), if desired, they may each be administered by different routes (that is, for example, one component of the combination product may be administered orally, and another component may be administered intravenously) or in different dosage forms (that is, for example, one component as a tablet and another as a liquid).

As will be appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of component (i) and component (ii) will be readily ascertainable by a medical practitioner skilled in the art, based upon the present disclosure. By way of general guidance, typically a daily dosage may be about 0.1 milligrams to about 1.5 grams of each component. By way of general guidance, when the compounds of component (i) and component (ii) are administered in combination, the dosage amount of each component may be reduced by about 70–80% relative to the usual dosage of the component when it is administered alone as a single agent for the treatment of abnormalities associated with low acetylcholine levels, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one or more of the active ingredients may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one or more of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one or more components is coated with a sustained and/or enteric release polymer, and the other(s) component is also coated with a polymer such as a low viscosity grade of hydroxypropyl methylcellulose or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredients are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of abnormal acetylcholine levels, which comprise a therapeutically effective amount of a compound of component (i) and a compound of component (ii) in one or more containers, are also within the ambit of the present invention. Sterilization of the container may be carried out using conventional sterilization methodology well known to those skilled in the art. Component (i) and component (ii) may be in the same container or in separate containers. The containers of materials may comprise separate containers, or one or more multi-part containers, as desired. Component (i) and component (ii) may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

EXAMPLE

The data below was developed using a microdialysis system to measure extracellular acetylcholine in a freely moving rat. Dialysis probes were placed in the dorsal hippocampus of rats and artificial csf was run though them. After an hour equilibration period, Samples of the dialysate were collected in 20 min intervals and assyed immediately for acetylcholine. Three samples were collected before the administration of test agents. The acetylcholine levels from these three samples served as baseline samples. Data are presented as % change from these baseline values. The compound 10,10-bis((2-fluoro-4-pyridinyl)methyl)- 9(10H) anthracenone (Cmpd.1) was administered at 0.5 mg/kg p.o. and donepezil HCl (Cmpd.2) was administered at 20 mg/kg p.o. The drugs when combined were administered at these same doses.

| Time (min) | vehicle | Cmpd. 1 | Cmpd. 2 | Combination |
|---|---|---|---|---|
| 20 | 6 | 19 | 54 | 35 |
| 40 | 8 | 20 | 41 | 65 |
| 60 | 2 | 0 | 49 | 67 |
| 80 | −7 | 2 | 33 | 54 |
| 100 | 9 | −6 | 28 | 52 |
| 120 | 3 | 2 | 21 | 57 |
| 140 | 3 | 18 | 31 | 44 |
| 160 | −2 | −2 | 31 | 42 |
| 180 | −4 | −3 | 29 | 48 |

The results shown above indicate that the effect of the combination of Cmpd.1 and Cmpd.2 was greater than the additive effect of each agent when administered alone.

What is claimed is:

1. A pharmaceutical composition comprising a therapeutically effective amount of a combination of:

(i) at least one neurotransmitter release enhancer having the formula:

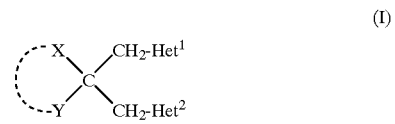

(I)

or a pharmaceutically acceptable salt thereof, wherein:
X and Y are taken together to form a saturated or unsaturated carbocyclic first ring and the shown carbon in said ring is α to at least one additional carbocyclic aromatic ring fused to the first ring, the total number of carbocyclic fused rings being 3–5, the sole heterocyclic substituents on said fused rings being $Het^1$ and $Het^2$; and
one of $Het^1$ or $Het^2$ is 2, 3, or 4-pyridyl or 2, 4, or 5-pyrimidinyl and the other is selected from
(a) 2, 3, or 4-pyridyl optionally substituted with a halogen atom or trifluoromethyl,
(b) 2, 4, or 5-pyrimidinyl,
(c) 2-pyrazinyl,
(d) 3 or 4-pyridazinyl,
(e) 3 or 4-pyrazolyl,
(f) 2 or 3-tetrahydrofuranyl, and
(g) 3-thienyl;
(ii) at least one acetylchlolinesterase inhibitor, and a pharmaceutically acceptable carrier.

2. A composition of claim 1 wherein said neurotransmitter release enhancer is a compound of the formula:

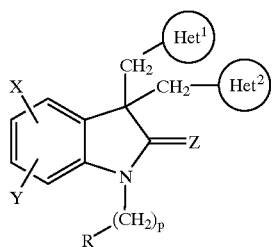

(Ia)

wherein:
p is 0 or 1;
Z is O or S;
R is $C_1$–$C_{10}$ alkyl, $C_3$–$C_8$ cycloalkyl, 2-pyridyl, 3-pyridyl, 4-pyridyl, or

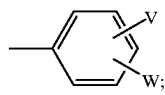

V,W,X, and Y independently are H, halo, $C_1$–$C_3$ alkyl, $OR^1$, $NO_2$, $CF_3$, CN or $NR^1R^2$;
$R^1$ and $R^2$ independently are H or $C_1$–$C_3$ alkyl;
$Het^1$ and $Het^2$ independently are 6-membered heterocyclic aromatic rings containing one or two nitrogen atoms as part of the ring optionally substituted with one substituent selected from the group $C_1$–$C_3$ alkyl, halo, $OR^1$ or $NR^1R^2$; or
an N-oxide or pharmaceutically acceptable acid addition salt thereof.

3. A composition of claim 1 wherein said neurotransmitter release enhancer is a compound of the formula:

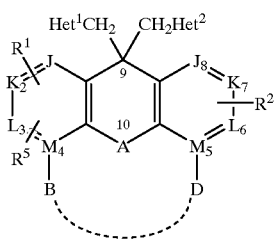

(Ib)

or a pharmaceutically acceptable salt thereof, wherein:
each J, K, L and M independently are N, $CR^1$, $CR^5$ or $CR^2$ with the proviso that when either $M_4$, $M_5$ or both is N, then B, D or both cannot be $R^1$ or $R^2$;
A is $(CH_2)_n$, C(=S), O, $S(O)_1$, $S(O)_2$, S, $NR^3$, —CH=CH—, —C(=O)—, —CH($OR^3$)—, C(=NOH)—,

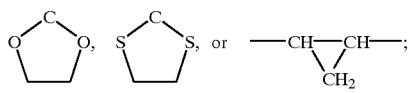

n is 0, 1, 2 or 3;
$R^1$ and $R^2$ independently are H, halo, alkyl of 2–3 carbon atoms, acetyl, $OR^3$, $NO_2$, CN, $NR^3R^4$, or fluoroalkyl of 1–3 carbon atoms;

$R^3$ and $R^4$ independently are H, alkyl of 1–3 carbon atoms, or acyl;
B and D independently are $R^1$ or $R^2$ or, when A is $(CH_2)_n$, can be taken together to form —CH=CH—, or —CH$_2$—CH$_2$—;
$R^5$ independently is H, or is taken together with $R^1$ to form a 2,3- or a 3,4-fused benzo ring;
one of $Het^1$ or $Het^2$ is 2, 3, or 4-pyridyl or 2, 4 or 5-pyrimidinyl and the other is selected from:
(a) 2, 3 or 4-pyridyl optionally substituted with a halogen atom or trifluoromethyl,
(b) 2, 4, or 5-pyrimidinyl,
(c) 2-pyrazinyl,
(d) 3 or 4-pyridazinyl,
(e) 3 or 4-pyrazolyl,
(f) 2 or 3-tetrahydrofuranyl, and
(g) 3-thienyl.

4. A composition of claim 1 wherein said acetylcholinesterase inhibitor is selected from the group consisting of tacrine and donepezil HCL.

5. A composition of claim 4 wherein the weight ratio of (i) to (ii) is in the range of 1:1 to 1:100.

6. A composition of claim 4 wherein said neurotransmitter release enhancer is selected from: 3,3-bis(4-pyridinylmethyl)-1-phenylindolin-2-one and 10,10-bis((2-fluoro-4-pyridinyl)methyl)-9(10H) anthracenone.

7. A method of treating a neurological or cognitive disorder in a mammal comprising administering to a mammal a therapeutically effective amount of a combination of:
(i) at least one neurotransmitter release enhancer having the formula:

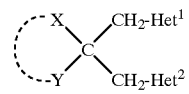

(I)

or a pharmaceutically acceptable salt thereof, wherein:
X and Y are taken together to form a saturated or unsaturated carbocyclic first ring and the shown carbon in said ring is α to at least one additional carbocyclic aromatic ring fused to the first ring, the total number of carbocyclic fused rings being 3–5, the sole heterocyclic substituents on said fused rings being $Het^1$ and $Het^2$; and
one of $Het^1$ or $Het^2$ is 2, 3, or 4-pyridyl or 2, 4, or 5-pyrimidinyl and the other is selected from
(a) 2, 3, or 4-pyridyl optionally substituted with a halogen atom or trifluoromethyl,
(b) 2, 4, or 5-pyrimidinyl,
(c) 2-pyrazinyl,
(d) 3 or 4-pyridazinyl,
(e) 3 or 4-pyrazolyl,
(f) 2 or 3-tetrahydrofuranyl, and
(g) 3-thienyl;
and (ii) at least one acetylcholinesterase inhibitor.

8. A method of claim 7 wherein said neurotransmitter release enhancer is a compound of the formula:

(Ia)

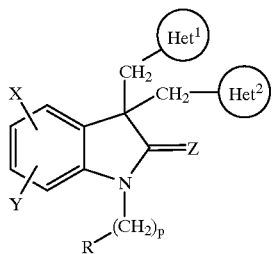

wherein:
p is 0 or 1;
Z is O or S;
R is $C_1$–$C_{10}$ alkyl, $C_3$–$C_8$ cycloalkyl, 2-pyridyl, 3-pyridyl, 4-pyridyl, or

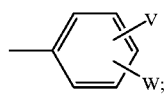

V, W, X, and Y independently are H, halo, $C_1$–$C_3$ alkyl, $OR^1$, $NO_2$, $CF_3$, CN or $NR^1R^2$;
$R^1$ and $R^2$ independently are H or $C_1$–$C_3$ alkyl;
$Het^1$ and $Het^2$ independently are 6-membered heterocyclic aromatic rings containing one or two nitrogen atoms as part of the ring optionally substituted with one substituent selected from the group $C_1$–$C_3$ alkyl, halo, $OR^1$ or $NR^1R^2$; or
an N-oxide or pharmaceutically acceptable acid addition salt thereof.

9. A method of claim 7 wherein said neurotransmitter release enhancer is a compound of the formula:

(Ib)

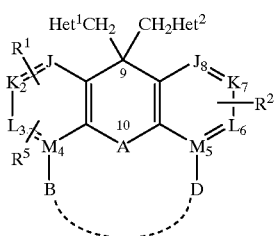

or a pharmaceutically acceptable salt thereof, wherein:
each J, K, L and M independently are N, $CR^1$, $CR^5$ or $CR^2$ with the proviso that when either $M_4$, $M_5$ or both is N, then B, D or both cannot be $R^1$ or $R^2$;
A is $(CH_2)_n$, C(=S), O, $S(O)_1$, $S(O)_2$, S, $NR^3$, —CH=CH—, —C(=O)—, —CH($OR^3$)—, C(=NOH)—,

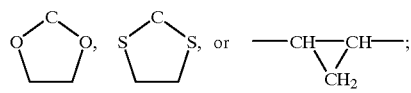

n is 0, 1, 2 or 3;
$R^1$ and $R^2$ independently are H, halo, alkyl of 2–3 carbon atoms, acetyl, $OR^3$, $NO_2$, CN, $NR^3R^4$, or fluoroalkyl of 1–3 carbon atoms;

$R^3$ and $R^4$ independently are H, alkyl of 1–3 carbon atoms, or acyl;
B and D independently are $R^1$ or $R^2$ or, when A is $(CH_2)_n$, can be taken together to form —CH=CH—, or —$CH_2$—$CH_2$—;
$R^5$ independently is H, or is taken together with $R^1$ to form a 2,3- or a 3,4-fused benzo ring;
one of $Het^1$ or $Het^2$ is 2, 3, or 4-pyridyl or 2, 4 or 5-pyrimidinyl and the other is selected from:
(a) 2, 3 or 4-pyridyl optionally substituted with a halogen atom or trifluoromethyl,
(b) 2, 4, or 5-pyrimidinyl,
(c) 2-pyrazinyl,
(d) 3 or 4-pyridazinyl,
(e) 3 or 4-pyrazolyl,
(f) 2 or 3-tetrahydrofuranyl, and
(g) 3-thienyl.

10. A method of treating a neurological or cognitive disorder in a mammal comprising administering a therapeutically effective amount of a combination of:
(i) a compound of the formula:

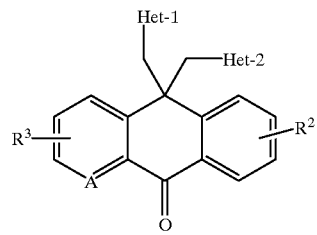

or a pharmaceutically acceptable salt thereof, wherein:
A is N or CH;
Het-1 and Het-2 are each independently selected from 2-pyridyl, 3-pyridyl or 4-pyridyl substituted with X;
$R^2$ and $R^3$ are independently selected from H, F, Cl, Br, I, $CF_3$, $R^4$, or —C≡CH;
$R^4$ is alkyl of 1 to 4 carbons;
X in each instance is independently selected from H, F, Cl, Br, I, or $CF_3$, provided that at least one X is other than H; and
(ii) an acetylcholinesterase inhibitor.

11. A method of claim 10 wherein Het-1 and Het-2 are independently 4-pyridyl substituted with X.

12. A method of claim 10 wherein A is CH.

13. A method of claim 10 wherein $R^2$ and $R^3$ are independently H, F, Br, or $CF_3$.

14. A method of claim 10, wherein one X is H and the other F; and $R^2$ and $R^3$ are each H.

15. A method of claim 10, wherein each X is F and $R^2$ and $R^3$ are each H.

16. A method of claim 10 wherein the neurotransmitter release enhancer is selected from: 10,10-bis((2-fluoro-4-pyridyl)methyl)-9(10H)-anthracenone; or 10-((2-fluoro-4-pyridyl)methyl)-10-(4-pyridylmethyl)-9(10)-anthracenone.

17. A method of claim 10 wherein the acetylcholinesterase inhibitor is donepezil HCl.

18. A method of claim 16 wherein the acetylcholinesterase inhibitor is donepezil HCl.

19. A method of claim 7 wherein said neurotransmitter release enhancer is selected from: 3,3-bis(4-pyridylmethyl)-1-phenylindolin-2-one and 10,10-bis((2-fluoro-4-pyridyl) methyl)-9(10H) anthracenone; and the acetylchlolinesterase inhibitor is donepezil HCl.

* * * * *